United States Patent [19]

Davis et al.

[11] Patent Number: 4,467,281

[45] Date of Patent: Aug. 21, 1984

[54] MULTI FREQUENCY EDDY CURRENT TEST APPARATUS WITH INTERMEDIATE FREQUENCY PROCESSING

[75] Inventors: Thomas J. Davis; Charles B. Perry, both of Richland, Wash.

[73] Assignee: Electric Power Research Institute, Inc., Palo Alto, Calif.

[21] Appl. No.: 125,895

[22] Filed: Feb. 29, 1980

[51] Int. Cl.³ .................. G01N 27/72; G01R 33/12
[52] U.S. Cl. ............................. 324/232; 324/233; 324/237; 332/9 R
[58] Field of Search ............... 324/227, 228, 232, 233, 324/241-243, 335, 340, 341, 237, 238, 79 R, 79 D; 332/9 R, 22

[56] References Cited

U.S. PATENT DOCUMENTS

| | | | |
|---|---|---|---|
| 3,626,279 | 12/1971 | Walden | 324/329 |
| 4,006,407 | 2/1977 | Flaherty et al. | 324/233 |
| 4,107,598 | 8/1978 | Meador et al. | 324/341 |
| 4,207,520 | 6/1980 | Flora et al. | 324/238 |

Primary Examiner—Gerard R. Strecker
Assistant Examiner—Walter E. Snow
Attorney, Agent, or Firm—Flehr, Hohbach, Test, Albritton & Herbert

[57] ABSTRACT

An eddy current test apparatus and method in which multiple sequential test frequencies are employed. The voltage induced in a sensing coil at said test frequencies are multiplexed and frequency translated to provide a single frequency for processing. The apparatus employs a single channel to process the induced voltages.

12 Claims, 6 Drawing Figures

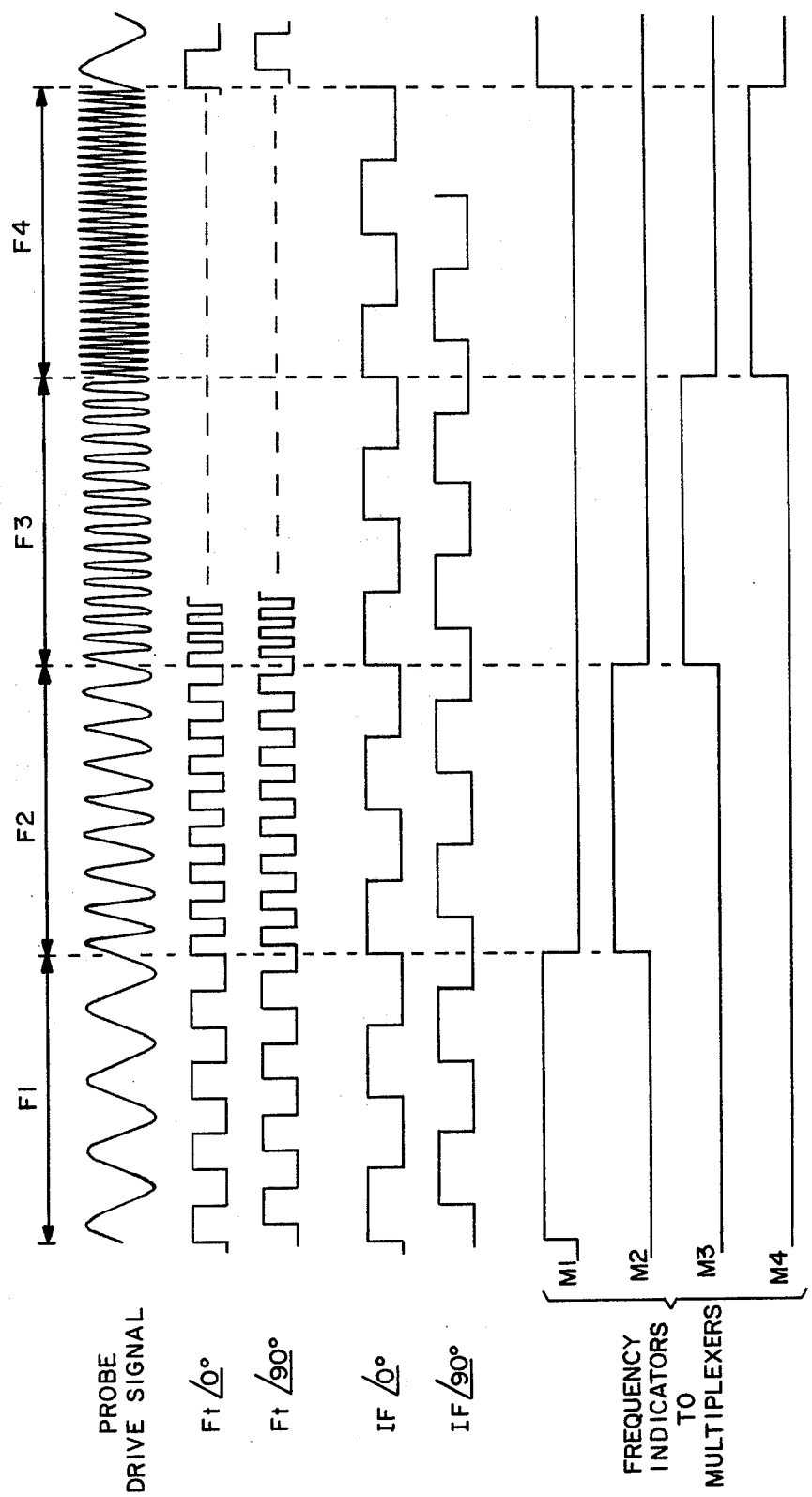

MULTI FREQUENCY EDDY CURRENT TEST APPARATUS WITH INTERMEDIATE FREQUENCY PROCESSING

This invention relates generally to an eddy current test apparatus and method and more particularly to such apparatus and method which employs multiplexing and frequency translation to provide an improved economical test apparatus.

The principles of electromagnetic non-destructive testing are well known. More particularly, in such tests, eddy currents are caused to flow within an object to be tested by induction from an adjacent coil which is excited by an alternating current. The eddy currents generate magnetic fields which couple to the coil and induce voltages within the coil which are at the same frequency as that of the excitation current but which may be at a different phase angle. The phase angle and amplitude of the induced voltages depend upon the characteristics of the object under test. The induced voltage may be measured by suitable electronic equipment which senses either a variation in voltage or equivalent impedance of the coil. Induced voltages vary with the test coil to object magnetic coupling and characteristics of the objects being scanned. Thus, changes in electrical conductivity, cracks, spacing of the coil and the like all modify the intensity of the eddy current as the coil is moved past the object under test. Changes in impedance or voltage due to the reflected eddy current magnetic field provide indications of the variations in spacing conductivity, cracks, etc. When employing single frequency testing it is virtually impossible to discriminate between the various parameters which cause the change in impedance or voltage. To overcome these problems, the coil has in the past been excited with a number of frequencies and the output signals combined to cancel out unwanted test parameters while retaining those of interest.

Multifrequency eddy current testing is generally implemented by simultaneously operating two or more single frequency instruments with a common probe or coil system. Two parameters $A_i$ and $B_i$ are output for each frequency, namely, the in-phase and quadrature components of the search coil impedance or voltages. These parameters $A_i$ and $B_i$ are the Fourier amplitude coefficients of the coil signal and are related to the eddy currents flowing in the test specimens as follows:

$$A \cos \omega t + B \sin \omega t = kH_s$$

where
  k is a proportionality factor;
  $H_s$ is the field generated by the eddy currents;
  $\omega$ the frequency; and
  t the time.

The parameters for each of the frequencies can then be mixed and combined to provide measurements of flaw locations, depth of the flaws, wall thickness and the like while eliminating unwanted parameters such as support signals and probe wobble signals. Suitable processing systems have been described in our copending application Ser. No. 49,192, filed June 18, 1979, entitled Multifrequency Eddy Current Test Apparatus and Method.

The present invention relates to a multifrequency instrument and does not deal with a combination process for elimination of unwanted parameters since those have been disclosed and discussed in the prior art and in the aforementioned pending application.

It is an object of the present invention to provide a multi-frequency eddy current test apparatus and method which employs multiplexing and frequency translation to permit testing with a single apparatus or channel.

It is another object of the present invention to provide a multi-frequency eddy current test apparatus and method which is simple and economical.

It is a further object of the present invention to provide a multi-frequency test apparatus and method in which the operating frequencies can be changed without retuning the apparatus.

The foregoing and other objects of the invention are achieved by an apparatus which sequentially gates test frequencies onto the search coil one at a time. The output of the probe containing the coils is subjected to a frequency translation process which converts all test frequencies to a common intermediate frequency for processing. The translated signal is then processed by a single channel of circuitry which amplifies the signal, automatically nulls prior to making measurements and detects the in-phase and quadrature components. The in-phase and quadrature components are stored in sample hole modules which are refreshed at the multiplex rate.

The invention is described in connection with the accompanying drawings in which:

FIG. 4 shows the signals applied to the coils and signals appearing at various points in the circuits of FIG. 1.

FIG. 5 shows the signals and waveforms occurring during frequency translation.

FIG. 6 shows the signals at the phase sensitive detectors.

Figure 1:
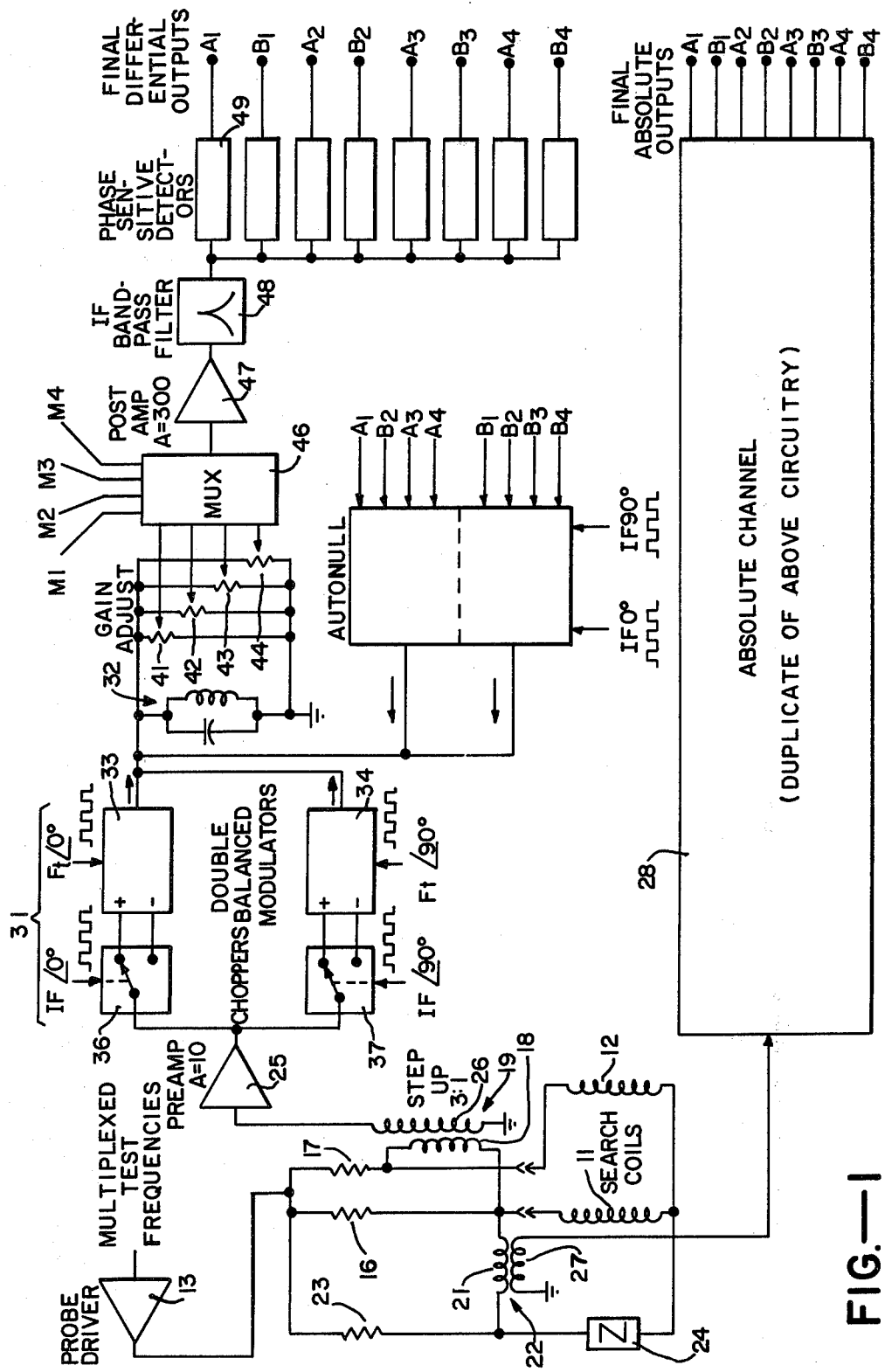
FIG. 1 is a block diagram showing a multi-frequency eddy current test apparatus in accordance with the present invention.

Referring to FIG. 1, there is illustrated a pair of search coils 11 and 12 which are excited by multiplexed test frequencies supplied through an amplifier 13. Coils 11 and 12 are connected in a first bridge circuit including resistors 16 and 17 with a differential output of the bridge circuit appearing at the primary 18 of transformer 19. The absolute output is supplied by a primary 21 of transformer 22. The primary 21 is connected across the legs of a bridge which includes the resistors 16 and 23, coil 11 and impedance 24. The test frequencies are supplied from a suitable source such as a plurality of oscillators and multiplexed as, for example, by gating so that they are applied sequentially to the probe. For example, there may be four test frequencies F1, F2, F3 and F4 sequentially applied to the test probe. By way of example, we have used the following test frequencies:

F1 = 25 kHz.
F2 = 200 kHz.
F3 = 400 kHz.
F4 = 1.6 MHz.

The differential bridge signal is extracted by the secondary 26 of the step-up transformer 19. The output is applied to a preamplifier 25 and then to frequency translation and associated circuitry in accordance with the present invention. Likewise, the output for the absolute channel is derived at the secondary 27 of the transformer 22 and applied to a preamplifier and circuitry identical to that to be described in connection with the differential channel and illustrated by the block 28. In each instance the final outputs are the complex Fourier parameters $A_i$ and $B_i$.

The amplified signal from the preamplifier 25 is applied to a chopper-modulator circuit combination 31 which performs frequency translation. The output of the modulators are current drive signals which are injected into a parallel resonant tank circuit 32. As will be presently described, the voltage developed across the tank circuit is 25 kHz intermediate frequency sinusoid whose phase and amplitude is the direct analog of the amplified bridge signal phase and amplitude.

The phase of the output signal from the preamplifier 25 applied to the double balanced modulators 33 and 34 is keyed between 0° and 180° by the choppers 36 and 37 respectively. The choppers 36 and 37 may be any suitable discrete circuit or integrated circuit choppers. For example, they may be integrated circuits sold by National Semiconductor and identified as their model number AH0014. The control signal to the choppers is an intermediate frequency (IF) having a frequency of 25 kHz illustrated and identified in FIG. 4. The IF applied to the choppers has a quadrature relationship IF∠0° and IF∠90°. The output of the chopper 36 is applied to double balance modulator 33 while the output of the chopper 37 is applied to the double balance modulator 34. The modulators may be of the type sold by National Semiconductor and identified as their Model No. LM1596 or an equivalent discrete or integrated circuit. The signal from the choppers is multiplied in the modulator by a squarewave at the test frequency. A typical squarewave signal is shown in FIG. 4 and can be obtained by processing the test signals by well known techniques. The output of the first modulator 33 is the probe signal multiplied by an in-phase squarewave of the test frequency, $F_t\angle 0°$, with its polarity being reversed in synchronism with the 25 kHz in-phase squarewave. This process is repeated in the second modulator chopper modulator combination with the chopping signal and the test frequency squarewave being delayed 90°, $F_t\angle 90°$. The output signals from the two modulators are summed and filtered in the tank circuit 32. The tank circuit filtering effect is such that only the 25 kHz components of the signal are present. The summing is a vector addition since the 25 kHz components of the two signals are at a 90° phase difference. The net result of this process is the generation of in-phase and quadrature 25 kHz signals whose amplitudes, respectively, are directly related to the in-phase and quadrature components of the bridge signal. The summation of these two signals generates a 25 kHz sinusoid whose phase and amplitude tracks that of the bridge signal. The modulation process is shown for the in-phase or 0° waves only in FIG. 5.

The frequency translation process may be mathematically explained using analog multiplication and all sinusoidal signals. This treatment is valid since the bandpass filtering in the present apparatus removes all but fundamental components of the signals. The following example shows how the in-phase components of the intermediate frequency is generated by multiplying three signals together. These signals are:

the amplified bridge signal: $E \sin(w_Tt+\phi)$
a sinusoid of the intermediate frequency: $F \sin w_It$
a sinusoid of the test frequency: $G \sin w_Tt$
Their product is:

$$(EFG/4) \sin(2w_Tt-w_It+\phi)-\sin(-w_It+\phi)-\sin(2W_Tt+\phi)+\sin(w_It+\phi) \quad (1)$$

After bandpass filtering at $w_I$, the remaining signal is:

$$(EFG/4) \sin(w_It+\phi)-\sin(-w_It+\phi) \quad (2)$$

This reduces to:

$$(EFG/2) \sin w_It \cdot \cos\phi \quad (3)$$

which is a sinusoid of the intermediate frequency whose amplitude is a function of the in-phase component of the bridge signal. The quadrature intermediate frequency component is:

$$(EFG/2) \cos w_It \cdot \sin\phi \quad (4)$$

and is derived by using cosines of the intermediate and test frequencies in the multiplication process.
The sum of (3) and (4) is:

$$(EFG/2) \cos(w_It+\phi) \quad (5)$$

preserving the amplitude E and the phase $\phi$ of the amplified bridge signal $E \sin(w_Tt+\phi)$.

The same multiplication process is performed by the chopper-modulator combinations except that the multiplicands are squarewaves. This eliminates the need to generate both sine and cosine waves and avoids the noise and limited bandwidth inherent in analog multipliers.

Figure 2:
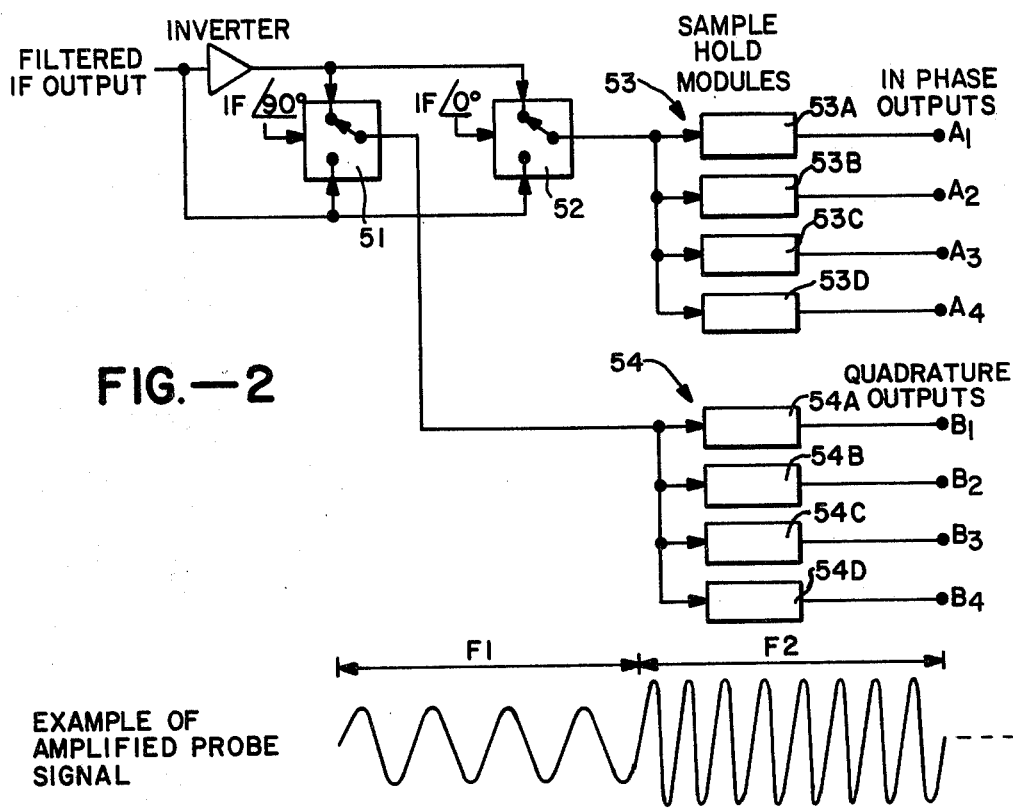
FIG. 2 is a block diagram of the phase sensitive detectors of FIG. 1.

The frequency translation takes place for each of the test frequencies sequentially with their outputs applied to the tank circuit 32 at the common intermediate frequency, 25 kHz. Thus, the signals must be sequentially removed from the tank circuit for detection by the phase sensitive detectors to provide the Fourier amplitude components $A_i$, $B_i$. Referring to FIG. 1, there are shown four voltage dividers comprising resistors 41, 42, 43 and 44 each with a variable tap to thereby provide for gain adjustment. The output from the resistors are applied to a multiplexer 46 which is responsive to the frequency indicator signals M1, M2, M3 and M4, FIG. 4. The multiplexer may be of the type sold by National Semiconductor and identified as their Model AH0015. The multiplexer is responsive to the input signals M1, M2, M3 and M4 to sequentially connect the amplifier 47 to the tank circuit to thereby amplify the respective signals. These signals are then passed through a bandpass filter which is tuned to the intermediate frequency and to phase sensitive detectors 49. Referring to FIG. 2, a more detailed block diagram of the phase sensitive detector array is shown. The phase sensitive detector array includes choppers 51 and 52 connected to receive directly the filtered output and the inverted filtered output and provide outputs to the sample and hold modules 53A-D and 54A-D. More particularly, chopper 51 is driven by the out-of-phase IF signal IF∠90° and serves to provide output to the sample and hold modules 54 while the chopper 52 is driven by the in-phase signals, IF∠0°, and applies its output to the sample and hold modules 53.

The sample and hold modules are used to detect the amplitude coefficients of the IF signals. The sample and hold circuits may be integrated circuits purchased from National Semiconductor, their number LH 0055 or any other suitable discrete or integrated circuit. A differential sampling scheme is used to suppress frequency response above and below the center frequency. This suppression is significant since the prior IF filtering must be done with very low Q circuits to avoid underdamped response from the multiplexing effect. Thus, additional band limiting in the sampling scheme further increases the signal-to-noise ratio. As described, the sampling scheme is first implemented by inverting the IF signal with choppers 51 and 52 driven by IF squarewaves. Two sample pulses per cycle of IF are applied to the command parts of the sample and hold modules. The IF∠0° chopped signal which is sampled by the modules is shown in FIG. 6 along with the sample pulses. A total of four samples are taken during a multiplexing interval for both the in-phase and quadrature components. Sample pulses are shown in the figure for the in-phase sample hold units. The pulses are located in the latter portion of the multiplexing interval so as to allow the IF signal to reach steady state condition before being sampled. Sample pulses for the quadrature unit are displaced 90° or a quarter period of the IF frequency away from those shown in this figure. The response time for the sample hold units is arranged so that the output is the average of the voltages present during the four sample pulses. Because of the chopper inverted input signals combined with averaging, the outputs are rendered less responsive to frequencies other than the intermediate frequencies and a bandpass response is achieved.

Prior to making measurements it is desirable to null the apparatus so that all outputs are zero. The autonull process is effected by generating in-phase and quadrature squarewaves of current at the intermediate frequency and injecting them into the tank circuit where all but the fundamental Fourier components are eliminated. The fundamental components of these waveforms are arranged to be equal but of opposite polarity to the IF signal so that the net sum of the waveforms is zero.

Figure 3:
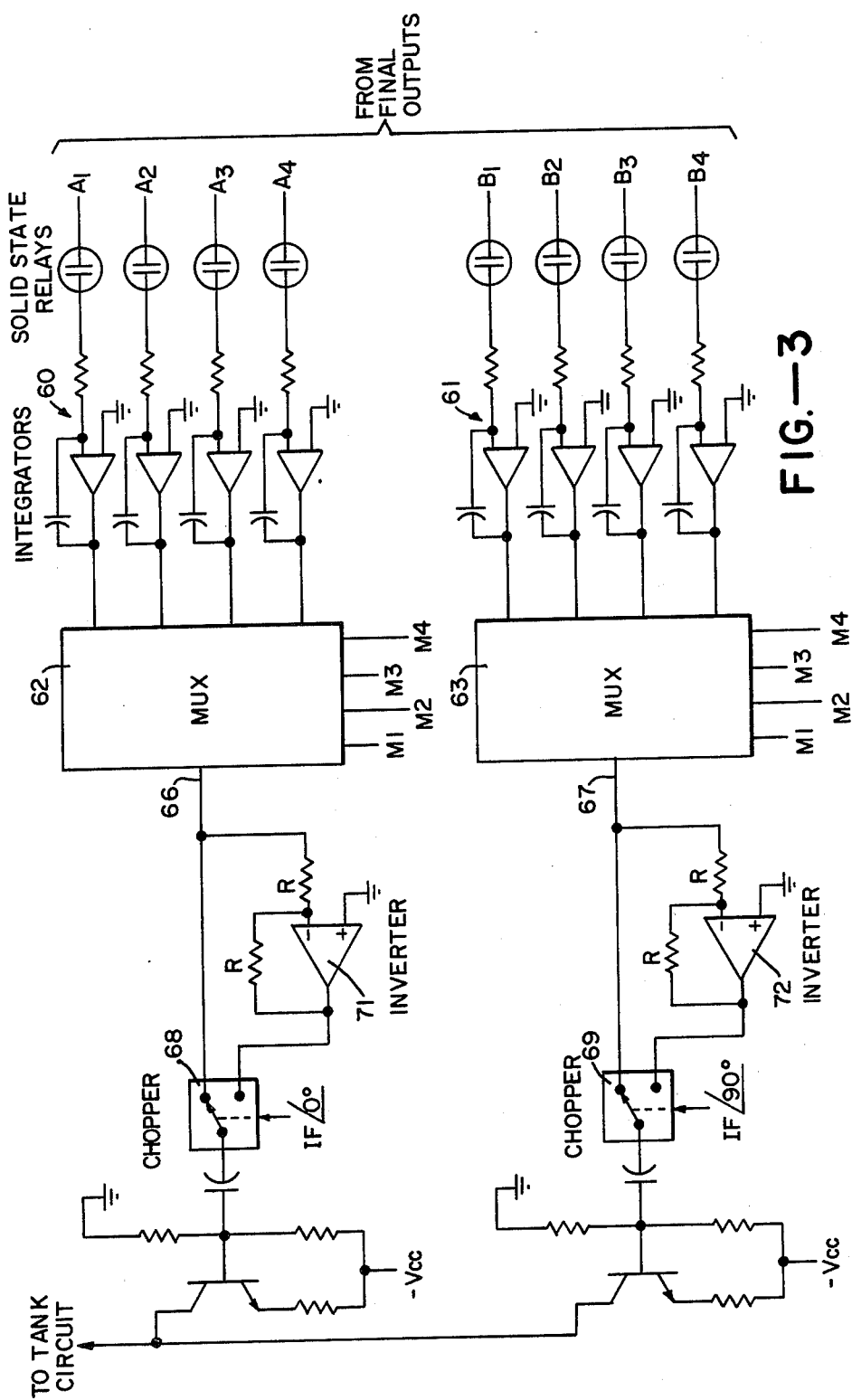
FIG. 3 is a block diagram of the autonull circuit of FIG. 1.

A block diagram of the autonull circuitry is shown in FIG. 3. Integrators 60, 61 serve as analog storage units to control the amplitude of the current squarewaves supplied to the multiplexers 62 and 63. The integrator outputs 60,60 are multiplexed onto a single channel 66,67 and then applied to choppers 68,69 which are operated at the IF frequency with one input being inverted by invertors 71,72, respectively. The outputs are amplified and applied to the tank circuit. The choppers operate at the intermediate frequency to form a voltage squarewave whose peak to peak amplitude is equal to the integrator output. The phase of the squarewave 0° or 180° is determined by the polarity of the integrator output. These in-phase and quadrature squarewaves are A-C coupled to a pair of transistors which serve as voltage to current convertors. The pair of analog multiplexers 62,63 connect the choppers to the appropriate integrator depending upon the test frequency. Autonulling occurs when the relay contacts shown are closed prior to carrying out a measurement. The integrators slew the tank circuit voltage until their outputs reach zero. The integrator output voltage required for zero input remains stored in the integrating capacitors after the contacts are opened.

Although described in connection with multiple frequency testing the conversion of test signals to an intermediate frequency is also useful in single frequency testing.

Thus, there has been provided a simple, economical eddy current test apparatus and method. By the frequency conversion and multiplexing processes disclosed, the apparatus is essentially a single channel apparatus.

What is claimed is:

1. Eddy current test apparatus including inducing coil means adapted to be coupled to an object to be tested to induce eddy currents in said object which currents induce voltages in sensing coil means, said induced voltages containing certain phase and amplitude information;

means for sequentially providing at least two test frequencies, one at a time, to said inducing coil means;

means for receiving and converting the induced voltages in said sensing coil means by said induced eddy currents to an intermediate frequency having a fixed predetermined frequency value independent of the frequency value of each test frequency selected while preserving said phase and amplitude information of said induced voltages, said converting means including first and second choppers and means for driving said first and second choppers at IF∠0° and at IF∠90°, respectively, where IF is the intermediate frequency; and means for sequentially processing said intermediate frequency to provide in-phase and quadrature components, $A_iB_i$ for each of the test frequencies.

2. Eddy current test apparatus as in claim 1 including first and second modulators connected to receive the outputs of the first and second choppers and means for driving the first one of modulators with a signal $F_T∠0°$ and the second with a signal $F_T∠90°$ where $F_T$ is the test frequency.

3. Eddy current test apparatus as in claim 2 including a resonant circuit connected to receive the output of said first and second modulators and to eliminate all but the fundamental components of these outputs said fundamental components being the in-phase and quadrature components of the intermediate frequency.

4. Eddy current test apparatus as in claim 3 including multiplex means responsive to control signals connected to said resonant circuit and serving to sequentially apply signals corresponding to each of the test frequencies to a signal processing circuit.

5. Eddy current test apparatus as in claim 4 wherein said signal processing apparatus includes phase sensitive detectors.

6. Eddy current test apparatus as in claim 5 wherein said phase sensitive detectors include third and fourth choppers driven at IF∠0° and IF∠90° where IF is the intermediate frequency to provide inverted and non-inverted signals and sample and hold circuits connected to receive the outputs of the choppers, one such sample and hold circuit for each test frequency to provide the in-phase and quadrature outputs $A_iB_i$.

7. Eddy current test apparatus as in claim 3 including means connected to receive said in-phase and quadrature outputs and serving to derive nulling signals for application to said resonant circuit.

8. Eddy current test apparatus as in claim 6 including means connected to receive said in-phase and quadrature outputs and serving to derive nulling signals for application to said resonant circuit.

9. Eddy current test apparatus as in claims 7 or 8 wherein said means connected to receive the in-phase and quadrature outputs and provide autonull signals to the resonant circuit comprises switching means serving to connect said outputs to the resonant circuit responsive to a command, integrators serving to receive said outputs and apply the same to first and second multiplexers, means for applying signals to said multiplexers to sequentially switch the signals $A_i$ and $B_i$, fifth and sixth choppers, connected to receive said signals, means for driving said choppers at IF$\angle 0°$ and IF$\angle 90°$ and amplifiers serving to apply the output of the choppers to the resonant circuit.

10. Eddy current test apparatus including inducing coil means adapted to be coupled to an object to be tested to induce eddy currents in said object which currents induce voltages in sensing coil means said induced voltages containing certain phase and amplitude information;

means for sequentially providing at least one test frequency to said inducing coil means;

means for receiving and converting the induced voltages in said sensing coil means by said induced eddy currents to an intermediate frequency having a predetermined fixed frequency value independent of the frequency value of the test frequency selected while preserving phase and amplitude information of said induced voltages, said converting means including first and second choppers and means for driving said first and second choppers at IF$\angle 0°$ and at IF$\angle 90°$, respectively, where IF is the intermediate frequency; and means for sequentially processing said intermediate frequency to provide in-phase and quadrature components, $A_iB_i$ for each of the test frequencies.

11. Eddy current test apparatus as in claim 10 including first and second modulators connected to receive the outputs of the first and second choppers and means for driving the first one of modulators with a signal $F_T\angle 0°$ and the second with a signal $F_T\angle 90°$ where $F_T$ is the test frequency.

12. Eddy current test apparatus as in claim 11 including a circuit connected to receive the output of said first and second modulators and serving to eliminate all but the fundamental components of the outputs.

* * * * *